United States Patent
Zheng et al.

(10) Patent No.: US 11,124,789 B2
(45) Date of Patent: *Sep. 21, 2021

(54) MULTIPLE LIGASE COMPOSITIONS, SYSTEMS, AND METHODS

(71) Applicant: RGENE, Inc., San Francisco, CA (US)

(72) Inventors: Yu Zheng, San Francisco, CA (US); Manqing Hong, San Francisco, CA (US)

(73) Assignee: RGENE, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/837,674

(22) Filed: Apr. 1, 2020

(65) Prior Publication Data
US 2020/0248166 A1   Aug. 6, 2020

Related U.S. Application Data

(63) Continuation of application No. 15/426,543, filed on Feb. 7, 2017, now Pat. No. 10,626,390.

(60) Provisional application No. 62/292,558, filed on Feb. 8, 2016.

(51) Int. Cl.
C12N 9/00 (2006.01)
(52) U.S. Cl.
CPC ........ *C12N 9/93* (2013.01); *C12Y 605/01001* (2013.01); *C12Y 605/01002* (2013.01)
(58) Field of Classification Search
None
See application file for complete search history.

(56) References Cited

U.S. PATENT DOCUMENTS

| | | | |
|---|---|---|---|
| 5,695,934 A | 12/1997 | Brenner | |
| 5,714,330 A | 2/1998 | Brenner et al. | |
| 5,750,341 A | 5/1998 | Macevicz | |
| 5,912,148 A | 6/1999 | Eggerding | |
| 6,130,073 A | 10/2000 | Eggerding | |
| 6,210,891 B1 | 4/2001 | Nyren et al. | |
| 6,258,568 B1 | 7/2001 | Nyren | |
| 6,306,597 B1 | 10/2001 | Macevicz | |
| 6,432,360 B1 | 8/2002 | Church | |
| 6,485,944 B1 | 11/2002 | Church et al. | |
| 6,511,803 B1 | 1/2003 | Church et al. | |
| 6,787,308 B2 | 9/2004 | Balasubramanian et al. | |
| 6,818,395 B1 | 11/2004 | Quake et al. | |
| 6,833,246 B2 | 12/2004 | Balasubramanian | |
| 6,911,345 B2 | 6/2005 | Quake et al. | |
| 6,969,488 B2 | 11/2005 | Bridgham et al. | |
| 7,115,400 B1 | 10/2006 | Adessi et al. | |
| 7,169,560 B2 | 1/2007 | Lapidus et al. | |
| 7,282,337 B1 | 10/2007 | Harris | |
| 7,329,492 B2 | 2/2008 | Hardin et al. | |
| 7,482,120 B2 | 1/2009 | Buzby | |
| 7,501,245 B2 | 3/2009 | Quake et al. | |
| 7,668,697 B2 | 2/2010 | Volkov et al. | |
| 8,697,408 B2 | 4/2014 | Kucera et al. | |
| 8,790,873 B2 | 7/2014 | Namsaraev et al. | |
| 10,683,542 B2 * | 6/2020 | Zwirko | C40B 40/06 |
| 2005/0130173 A1 | 6/2005 | Leamon et al. | |
| 2008/0241951 A1 | 10/2008 | Battulga et al. | |
| 2009/0026082 A1 | 1/2009 | Rothberg et al. | |
| 2009/0035777 A1 | 2/2009 | Kokoris et al. | |
| 2009/0127589 A1 | 5/2009 | Rothberg et al. | |
| 2010/0137143 A1 | 6/2010 | Rothberg et al. | |
| 2010/0188073 A1 | 7/2010 | Rothberg et al. | |
| 2010/0197507 A1 | 8/2010 | Rothberg et al. | |
| 2010/0301398 A1 | 12/2010 | Rothberg et al. | |
| 2014/0187447 A1 | 7/2014 | Kucera et al. | |
| 2015/0011399 A1 | 1/2015 | Namsaraev et al. | |
| 2015/0031026 A1 | 1/2015 | Hendricks et al. | |

FOREIGN PATENT DOCUMENTS

| | | |
|---|---|---|
| WO | 2000/018957 A1 | 4/2000 |
| WO | 2006/084132 A2 | 8/2006 |
| WO | 2010/094040 A1 | 8/2010 |
| WO | 2018/140695 A1 | 8/2018 |

OTHER PUBLICATIONS

Adessi et al., "Solid phase DNA amplification: characterisation of primer attachment and amplification mechanisms," Nucleic Acid Res, 2000, 28: E87.
Arabshahi et al., "Standard free energy for the hydrolysis of adenylylated T4 DNA ligase and the apparent pKa of lysine 159," Journal of Biological Chemistry, 1999, 274(13):8586-8588.
Astier et al., "Toward single molecule DNA sequencing: direct identification of ribonucleoside and deoxyribonucleoside 5′-monophosphates by using an engineered protein nanopore equipped with a molecular adapter," J Am Chem Soc, 2006, 128(5): 1705-10.
Brenner et al., "Gene expression analysis by massively parallel signature sequencing (MPSS) on microbead arrays," Nat Biotechnol, 2000, 18: 630-634.
Clark, "Novel non-templated nucleotide addition reactions catalyzed by procaryotic and eucaryotic DNA polymerases," Nucleic Acids Res, 1988, 16(20): 9677-86.
Hafner et al., "Identification of microRNAs and Other Small Regulatory RNAs Using cDNA Library Sequencing," Methods, 2008, 44(1): 3-12.

(Continued)

*Primary Examiner* — Richard G Hutson
(74) *Attorney, Agent, or Firm* — Michael Best & Friedrich LLP

(57) ABSTRACT

Provided herein are compositions, systems, and methods using multiple ligases, wherein at least one of the ligases is an adenylation-deficient ATP-dependent ligase or an un-adenylated ATP-dependent ligase (e.g., present in an ATP free mixture). In certain embodiments, multiple ligases are used to ligate a pre-adenylated double stranded sequence to a non-adenylated double stranded sequence (e.g., the adenylation-deficient ATP-dependent ligase or un-adenylated ATP-dependent ligase ligates the first strand, and a second ligase ligates the second strand). In other embodiments, provided herein are mutant T4 ligases (e.g., K159S mutant or K159C mutant).

3 Claims, 8 Drawing Sheets

Specification includes a Sequence Listing.

(56) References Cited

OTHER PUBLICATIONS

International Search Report and Written Opinion for Application No. PCT/US2017/016812 dated Apr. 28, 2017 (12 pages).
Islam, "Efficient Ligation of DNA on RNA Templates using a Mutated T4 DNA Ligase," Master Thesis, Uppsala University, 2008.
Lau et al., "An abundant class of tiny RNAs with probable regulatory roles in Caenorhabditis elegans," Science, 2001, 294(5543): 858-62.
Lehman, "DNA ligase: structure, mechanism, and function," Science, 1974, 186(4166): 790-7.
Lindahl et al., "Mammalian DNA ligases," Annu Rev Biochem, 1992, 61: 251-81.
Lohman et al., "Kinetic characterization of single strand break ligation in duplex DNA by T4 DNA ligase," J Biol Chem, 2011, 286(51): 44187-96.
MacLean et al., "Application of 'next-generation' sequencing technologies to microbial genetics," Nature Rev Microbiol, 7: 287-296.
Magnuson et al., "Substrate nucleotide-determined non-templated addition of adenine by Taq DNA polymerase: implications for PCR-based genotyping and cloning," Biotechniques, 1996, 21(4): 700-9.
Margulies et al., "Genome sequencing in microfabricated high-density picolitre reactors," Nature, 2005, 437: 376-380.
Mitra et al., "Fluorescent in situ sequencing on polymerase colonies," Analytical Biochemistry, 2003, 320: 55-65.
Morozova et al., "Applications of next-generation sequencing technologies in functional genomics," Genomics, 2008, 92: 255-264.
Ngo et al., The Protein Folding Problem and Tertiary Structure Prediction, 1994, Merz et al. (ed.), Birkhauser, Boston, MA, pp. 433 and 492-495.
Pennisi et al., "Semiconductors Inspire New Sequencing Technologies," Science, 2010, 327(5970): 1190.
Rossi et al., "Functional Characterization of the T4 DNA Ligase: a New Insight into the Mechanism of Action," Nucleic Acids Research, 1997, 25(11): 2106-2113.
Sgaramella et al., "Studies on polynucleotides. CXVI. A further study of the T4 ligase-catalyzed joining of DNA at base-paired ends," J Mol Biol, 1972, 72(3): 493-502.
Shendure et al., "Accurate multiplex polony sequencing of an evolved bacterial genome," Science, 2005, 309: 1728-1732.
Shuman et al., "RNA capping enzyme and DNA ligase: a superfamily of covalent nucleotidyl transferases," Mol Microbial, 1995, 17(3): 405-10.
Shuman, "DNA ligases: progress and prospects," J Biol Chem, 2009, 284(26): 17365-9.
Sriskanda et al., "Chlorella virus DNA ligase: nick recognition and mutational analysis," Nucleic Acids Research, 1998, 26(2): 525-531.
Takahashi et al., "Activity-based in vitro selection of T4 DNA ligase," Biochemical and Biophysical Research Communications, 2005, 336(3):987-993.
Tomkinson et al., "DNA ligases: structure, reaction mechanism, and function," Chem Rev, 2006, 106(2): 687-99.
Torchia et al., "Archaeal RNA ligase is a homodimeric protein that catalyzes intramolecular ligation of single-stranded RNA and DNA," Nucleic Acids Res, 2008, 36(19): 6218-27.
Voelkerding et al., "Next-generation sequencing: from basic research to diagnostics," Clinical Chem, 2009, 55: 641-658.
Wang et al., "Human DNA ligase IV and the ligase IV/XRCC4 complex: analysis of nick ligation fidelity," Biochemistry, 2007, 46(17): 4962-76.
Weiss et al., "Enzymatic breakage and joining of deoxyribonucleic acid, I. Repair of single-strand breaks in DNA by an anzyme system from *Escherichia coli* infected with T4 bacteriophage," Proc Natl Acad Sci USA, 1967, 57(4): 1021-1028.
Yin et al., "Structure-Function Analysis of T4 RNA Ligase 2," J Biol Chem, 2003, 278: 17601-17608.
Zhelkovsky et al., "Structure-function analysis of Methanobacterium thermoautotrophicum RNA ligase—engineering a thermostable ATP independent enzyme," BMC Mol Biol, 2012, 13: 24.
European Patent Office Partial Supplementary Search Report for Application No. 17750627.6 dated Mar. 19, 2019 (15 pages).
European Patent Office Extended Search Report for Application No. 17750627.6 dated Jun. 21, 2019 (12 pages).
Japanese Patent Office Action for Application No. 2018-560726 dated Jul. 7, 2020 (4 pages, English translation included).
Japanese Patent Office Action for Application No. 2018-560726 dated Feb. 24, 2021 (4 pages including English translation).
China National Intellectual Property Administration First Office Action for Application No. 201780015885.4 dated Apr. 25, 2021 (25 pages including English translation).
European Patent Office Extended Search Report for Application No. 20217958.6 dated Jun. 15, 2021 (10 pages).

\* cited by examiner

FIG. 6

T4 DNA ligase K159S mutant (SEQ ID NO:1)

MILKILNEIASIGSTKQKQAILEKNKDNELLKRVYRLTYSRGLQYYIKKWPKPGIATQSF
GMLTLTDMLDFIEFTLATRKLTGNAAIEELTGYITDGKKDDVEVLRRVMMRDLECGASVS
IANKVWPGLIPEQPQMLASSYDEKGINKNIKFPAFAQLSADGARCFAEVRGDELDDVRLL
SRAGNEYLGLDLLKEELIKMTAEARQIHPEGVLIDGELVYHEQVKKEPEGLDFLFDAYPE
NSKAKEFAEVAESRTASNGIANKSLKGTISEKEAQCMKFQVWDYVPLVEIYSLPAFRLKY
DVRFSKLEQMTSGYDKVILIENQVVNNLDEAKVIYKKYIDQGLEGIILKNIDGLWENARS
KNLYKFKEVIDVDLKIVGIYPHRKDPTKAGGFILESECGKIKVNAGSGLKDKAGVKSHEL
DRTRIMENQNYYIGKILECECNGWLKSDGRTDYVKLFLPIAIRLREDKTKANTFEDVFGD
FHEVTGL

FIG. 7

T4 DNA ligase K159C mutant (SEQ ID NO:2)

MILKILNEIASIGSTKQKQAILEKNKDNELLKRVYRLTYSRGLQYYIKKWPKPGIATQSF
GMLTLTDMLDFIEFTLATRKLTGNAAIEELTGYITDGKKDDVEVLRRVMMRDLECGASVS
IANKVWPGLIPEQPQMLASSYDEKGINKNIKFPAFAQLCADGARCFAEVRGDELDDVRLL
SRAGNEYLGLDLLKEELIKMTAEARQIHPEGVLIDGELVYHEQVKKEPEGLDFLFDAYPE
NSKAKEFAEVAESRTASNGIANKSLKGTISEKEAQCMKFQVWDYVPLVEIYSLPAFRLKY
DVRFSKLEQMTSGYDKVILIENQVVNNLDEAKVIYKKYIDQGLEGIILKNIDGLWENARS
KNLYKFKEVIDVDLKIVGIYPHRKDPTKAGGFILESECGKIKVNAGSGLKDKAGVKSHEL
DRTRIMENQNYYIGKILECECNGWLKSDGRTDYVKLFLPIAIRLREDKTKANTFEDVFGD
FHEVTGL

FIG. 8

T4 DNA ligase K159A mutant (SEQ ID NO:3)

MILKILNEIASIGSTKQKQAILEKNKDNELLKRVYRLTYSRGLQYYIKKWPKPGIATQSF
GMLTLTDMLDFIEFTLATRKLTGNAAIEELTGYITDGKKDDVEVLRRVMMRDLECGASVS
IANKVWPGLIPEQPQMLASSYDEKGINKNIKFPAFAQLAADGARCFAEVRGDELDDVRLL
SRAGNEYLGLDLLKEELIKMTAEARQIHPEGVLIDGELVYHEQVKKEPEGLDFLFDAYPE
NSKAKEFAEVAESRTASNGIANKSLKGTISEKEAQCMKFQVWDYVPLVEIYSLPAFRLKY
DVRFSKLEQMTSGYDKVILIENQVVNNLDEAKVIYKKYIDQGLEGIILKNIDGLWENARS
KNLYKFKEVIDVDLKIVGIYPHRKDPTKAGGFILESECGKIKVNAGSGLKDKAGVKSHEL
DRTRIMENQNYYIGKILECECNGWLKSDGRTDYVKLFLPIAIRLREDKTKANTFEDVFGD
FHEVTGL

MULTIPLE LIGASE COMPOSITIONS, SYSTEMS, AND METHODS

CROSS-REFERENCE TO RELATED APPLICATION(S)

This application is a continuation of U.S. patent application Ser. No. 15/426,543, filed on Feb. 7, 2017, which claims priority to U.S. Provisional Patent Application No. 62/292,558, filed on Feb. 8, 2016, the entire contents of each of which are fully incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 18,972 bytes ASCII (Text) file named "013670-9044-US03-SEQ-LIST-04-01-20.txt," created on Apr. 1, 2020.

FIELD

Provided herein are compositions, systems, and methods using multiple ligases, wherein at least one of the ligases is an adenylation-deficient ATP-dependent ligase or an un-adenylated ATP-dependent ligase (e.g., present in an ATP free mixture). In certain embodiments, multiple ligases are used to ligate a pre-adenylated double stranded sequence to a non-adenylated double stranded sequence (e.g., the adenylation-deficient ATP-dependent ligase or un-adenylated ATP-dependent ligase ligates the first strand, and a different ligase ligates the second strand). In other embodiments, provided herein are mutant T4 ligases (e.g., K159S mutant or K159C mutant).

BACKGROUND

DNA ligases are divalent metal ion dependent enzymes that utilize ATP or NAD+ to catalyze phosphodiester bond formation between adjacent polynucleotide termini possessing a 3'-hydroxyl and a 5'-phosphate (Tomkinson A E, PNAS, 2006). DNA ligases are essential enzymes for DNA replication and repair and are universally found in eukaryotes, bacteria, archaea and many viruses. Depending on their origin of species, natural occurring DNA ligases may have many unique properties, for example, substrate specificity, sequence and domain organization, optimal reaction condition such as pH, temperature and salt tolerance.

All known DNA ligases perform the catalysis via a common pathway which involves three nucleotidyl transfer reactions (see, Lehman I R. et al, Science, 1974; and Lindahl T et al, Annu Rev Biochem, 1992; both of which are herein incorporated by reference in their entireties, particularly for the steps for ligation). In the case of ATP-dependent DNA ligases, the first step (step 1) involves the attack on the α-phosphate of ATP by ligase, which results in release of pyrophosphate and formation of a ligase-AMP intermediate. AMP is linked covalently to the amino group of a lysine residue within a conserved sequence motif. In the second step (step 2), the AMP nucleotide is transferred to the 5'-phosphate-terminated DNA strand to form a 5'-App-DNA intermediate. In the third and final step (step 3), attack by the 3'-OH strand on the 5'-App-DNA joins the two polynucleotides and liberates AMP.

T4 DNA ligase was one of the first DNA ligases isolated (Weiss B, et al, PNAS, 1967), and the enzyme has since been widely used as a tool in molecular biology applications as well as molecular diagnostics, including cloning, sequencing, and gene synthesis etc. T4 DNA ligase readily accepts both nicked double-stranded DNA and double-stranded breaks with complementary base pairing. Furthermore, it is unique in its ability to join DNA fragments with blunt ends or single-base overhangs, even in the absence of a ligation enhancer, such as polyethylene glycol (PEG) or other small molecules (see, Sogaramella V et al, JMB, 1972; U.S. Pat. No. 8,697,408). For this reason, T4 DNA ligase is routinely used in many in vitro applications such as the library preparation workflow for high-throughput sequencing or next-generation sequencing (NGS sequencing).

It is common in many molecular biology applications to ligate double-stranded oligonucleotide adaptors to a library of double-stranded DNA fragments. For example, adapter ligation is an important step in the library preparation workflow of NGS sequencing. Attachment of double-stranded oligonucleotides with designed and known sequences to a library of DNA fragments with unknown sequences facilitates downstream manipulations, such as PCR amplification or primer extension. Efficient and complete ligation step ensures the success of the library preparation, and can reduce the number of cycles required for the PCR amplification of the library, which helps to reduce the necessary amount of starting material and minimize the bias in the resulting sequencing data. For these reasons, there is a need for improvement of the efficiency and completeness of the ligation reaction for many applications.

SUMMARY

Provided herein are compositions, systems, kits, and methods using multiple different ligases, wherein at least one of the ligases is an adenylation-deficient ATP-dependent ligase or an un-adenylated ATP-dependent ligase (e.g., present in an ATP free mixture). In certain embodiments, multiple ligases are used to ligate a pre-adenylated double stranded sequence to a non-adenylated double stranded sequence (e.g., the adenylation-deficient ATP-dependent ligase or un-adenylated ATP-dependent ligase ligates the first strand, and a different ligase ligates the second strand). In other embodiments, provided herein are mutant T4 ligases (e.g., K159S mutant or K159C mutant).

In some embodiments, provided herein are compositions (e.g., in vitro compositions) comprising: a) a first ligase comprising an adenylation-deficient ATP-dependent ligase (i.e., a ligase that cannot form the AMP-ligase intermediate by reacting with ATP); and b) a second ligase, wherein the second ligase is: i) an ATP-dependent ligase, or ii) a NAD-dependent ligase. In certain embodiments, the first and/or second ligases are recombinantly produced. In certain embodiments, the first and second ligases can be fused into one single polypeptide and recombinantly produced. In certain embodiments, said composition is free or substantially free of biological molecules besides said first and second ligases (e.g., the composition consists essentially of the first and second ligases only, without other biological molecules, with the possible exception of target nucleic acid sequences to be ligated).

In certain embodiments, provided herein are compositions comprising a fusion protein, wherein the fusion protein comprises: a) a first ligase comprising an adenylation-deficient ATP-dependent ligase (i.e., a ligase that cannot form the AMP-ligase intermediate by reacting with ATP); and b) a second ligase, wherein the second ligase is: i) an ATP-dependent ligase, or ii) a NAD-dependent ligase.

In some embodiments, provided herein are compositions comprising: a) an un-adenylated ATP-dependent ligase; and b) a NAD-dependent ligase, and wherein the composition is free of, or detectably free of, adenosine tri-phosphate (ATP). In certain embodiments, the un-adenylated ATP-dependent ligase and/or NAD-dependent ligase are recombinantly produced.

In some embodiments, provided herein are systems and/or kits comprising: a) a first container containing a first composition comprising a first ligase, wherein the first ligase is: i) an adenylation-deficient ATP-dependent ligase, or ii) an un-adenylated ATP-dependent ligase, and wherein the first composition is free, or detectably free, of adenosine tri-phosphate (ATP) if the un-adenylated ATP-dependent ligase is present in the first composition; and b) a second container containing a second composition comprising a second ligase, wherein the second ligase is: i) an ATP-dependent ligase, or ii) a NAD-dependent ligase. In certain embodiments, the first and/or second ligases are recombinantly produced.

In some embodiments, provided herein are methods of ligating a nucleic acid sequence comprising: a) combining the following components into a reaction mixture: i) a first ligase, wherein the first ligase is: A) an adenylation-deficient ATP-dependent ligase, or B) an un-adenylated ATP-dependent ligase, and wherein the reaction mixture is free, or detectably free, of adenosine tri-phosphate (ATP) if the un-adenylated ATP-dependent ligase is present in the reaction mixture, ii) an adenylated double-stranded nucleic acid sequence (ADSNAS) (e.g., with blunt ends or with overhangs, such as sticky ends or single base overhangs), and iii) a non-adenylated double stranded nucleic acid sequence (non-ADSNAS) (e.g., with blunt ends or with overhangs, such as sticky ends or single base overhangs), wherein the non-ADSNAS comprises a first strand hybridized to a second strand (or where the non-ADSNAS is provided as first and second separate single strands hybridizable to each other), wherein the combining the components is under conditions such that the first ligase ligates the first strand of the non-ADSNAS to the ADSNAS (i.e. to the first, adenylated strand of the ADSNA), and b) adding a second ligase to the reaction mixture under conditions such that the second ligase ligates the second strand of the non-ADSNAS to the ADSNAS (i.e., to the second strand of the ADSNA), wherein the second ligase is: i) an ATP-dependent ligase, or ii) a NAD-dependent ligase. In particular embodiments, the methods further comprise subjecting the nucleic acid molecule formed by ligating the ADSNAS to the non-ADSNAS to a sequencing reaction to determine at least part of the nucleic acid sequence molecule (e.g., using a sequencing methodology that employs adapters ligated to library fragments).

In some embodiments, provided herein are methods of ligating a nucleic acid sequence comprising: combining the following components into a reaction mixture: a) a first ligase, wherein the first ligase is: i) an adenylation-deficient ATP-dependent ligase, or ii) an un adenylated ATP-dependent ligase, and wherein the reaction mixture is free, or detectably free, of adenosine tri-phosphate (ATP) if the un-adenylated ATP-dependent ligase is present in the reaction mixture, b) a second ligase, wherein the second ligase is a NAD-dependent ligase, c) an adenylated double-stranded nucleic acid sequence (ADSNAS), d) a non-adenylated double stranded nucleic acid sequence (non-ADSNAS), and wherein the combining the components is under conditions such that the first ligase ligates the first strand of the non-ADSNAS to the ADSNAS, and the second ligase ligates the second strand of the non-ADSNAS to the ADSNAS. In particular embodiments, the method further comprises subjecting the nucleic acid molecule formed by ligating the ADSNAS to the non-ADSNAS to a sequencing reaction to determine at least part of the nucleic acid sequence molecule.

In certain embodiments, the un-adenylated ATP-dependent ligase is selected from the group consisting of: T4 DNA ligase, T7 DNA ligase, T3 DNA ligase, and PBCV-1 DNA ligase, or their apparent close homologs. In other embodiments, the NAD-dependent ligase is selected from the group consisting of: *E. coli* DNA ligase, *Thermus thermophiles* DNA ligase, and *Thermus aquaticus* DNA ligase, or their apparent close homologs.

In certain embodiments, the compositions further comprise an adenylated double-stranded nucleic acid sequence (ADSNAS) (e.g., as shown in FIGS. 2 and 3; and which may be two separate sequences hybridized together or a single strand hairpin hybridized to itself). In particular embodiments, the ADSNAS is between 5 and 2000 base-pairs in length (e.g., 5 . . . 15 . . . 35 . . . 300 . . . 500 . . . 1000 . . . or 2000 base-pairs in length). In some embodiments, the ADSNAS comprises a detectable label or internal label. In other embodiments, the compositions further comprise a non-adenylated double stranded nucleic acid sequence (non-ADSNAS). In certain embodiments, the non-ADSNAS comprises a first strand hybridized to a second strand, and wherein the first strand can be ligated to the ADSNAS by the first ligase and the second strand can be ligated to the ADSNAS by the second ligase. In particular embodiments, the non-ADSNAS is between 5 and 4000 base-pairs in length (e.g., 5 . . . 15 . . . 35 . . . 300 . . . 500 . . . 2000 . . . or 4000 base-pairs in length). In particular embodiments, the non-ADSNAS codes for a protein or a portion of a protein. In some embodiments, the ADSNAS comprises a double stranded sequencing adapter (e.g., Illumina TRUSEQ adapter, Illumina NEXTERA adapter, SOLEXA sequencing adapter, ROCHE 454 sequencing adapter, SOLID sequencing adapter, and an ION XPRESS barcode adapter for ION TORRENT). In particular embodiments, the non-ADSNAS comprises a sequencing library fragment or other nucleic acid sequence of interest.

In particular embodiments, the first ligase (the adenylation-deficient ligase) comprises a mutant of a wild-type ligase. In particular embodiments, the first ligase comprises a mutant of a wild-type ligase having a Kx(D/N)G motif (wherein x is any amino acid), and wherein the mutant comprises the Kx(D/N)G motif except lysine in the motif is substituted for a different amino acid that causes the mutant to be adenylation deficient but still step 3 ligation capable. In particular embodiments, the mutant comprises a lysine-substituted motif selected from the group consisting of: Gx(D/N)G (SEQ ID NO:5), Px(D/N)G (SEQ ID NO:6), Ax(D/N)G (SEQ ID NO:7), Vx(D/N)G (SEQ ID NO:8), Lx(D/N)G (SEQ ID NO:9), Ix(D/N)G (SEQ ID NO:10), Mx(D/N)G (SEQ ID NO:11), Cx(D/N)G (SEQ ID NO:12), Fx(D/N)G (SEQ ID NO:13), Yx(D/N)G (SEQ ID NO:14), Wx(D/N)G (SEQ ID NO:15), Hx(D/N)G (SEQ ID NO:16), Rx(D/N)G (SEQ ID NO:17), Qx(D/N)G (SEQ ID NO:18), Nx(D/N)G (SEQ ID NO:19), Ex(D/N)G (SEQ ID NO:20), Dx(D/N)G (SEQ ID NO:21), Sx(D/N)G (SEQ ID NO:22), Tx(D/N)G (SEQ ID NO:23) and x(D/N)G (SEQ ID NO:24, point deletion of lysine); wherein x is any amino acid, and wherein N is asparagine.

In certain embodiments, the mutant comprises a mutant T4 DNA ligase (e.g., has an amino acid change from lysine at position 159). In particular embodiments, the mutant T4

DNA ligase is selected from the group consisting of: the K159S mutant, the K159C mutant, and the K159A mutant (e.g., as shown in SEQ ID NOS:1-3, or variants of these sequences having 97-99% identity with these sequences, or having N or C terminal truncations of these sequences that do not substantially alter the normal step 3 ligase activity). In particular embodiments, the T4 DNA ligase is encoded by SEQ ID NOS:1-3, but with one amino acid change (not at position 159) that does not substantially alter the ligase step 3 activity. In certain embodiments, the first ligase is the K27A mutant from *Chlorella* virus PBCV-1 DNA ligase (see, Sriskana et al., Nucleic Acids Research, 1998, 26(2), 525-531, which is herein incorporated by reference in its entirety, particularly with references to the K27A mutant).

In some embodiments, the second ligase is the ATP-dependent ligase, and wherein the ATP-dependent ligase is selected from the group consisting of: T4 DNA ligase, T7 DNA ligase, T3 DNA ligase, and PBCV-1 DNA ligase. In further embodiments, the second ligase is the NAD-dependent ligase, and wherein the NAD-dependent ligase is selected from the group consisting of: *E. coli* DNA ligase, *Thermus thermophiles* DNA ligase, and *Thermus aquaticus* DNA ligase.

In certain embodiments, provided herein are systems and kits comprising: a) a first container comprising a first composition comprising a T4 DNA ligase K159S mutant and/or a T4 DNA ligase K159C mutant; and b) a second container comprising a second composition comprising an adenylated double-stranded nucleic acid sequence (ADS-NAS). In certain embodiments, both the first and second containers are present in a package (e.g., a box or other shipping container). In particular embodiments, provided herein are compositions comprising: a T4 DNA ligase K159S mutant and/or a T4 DNA ligase K159C mutant.

In certain embodiments, the K159S mutant is encoded by the amino acid sequence SEQ ID NO:1 or a variant of this sequences having 97-99% identity with this sequence, or having an N or C terminal truncation of this sequence that does not substantially alter the normal ligase step 3 activity. In some embodiments, the T4 DNA ligase is encoded by SEQ ID NO: 1, but with one amino acid change (not at position 159) that does not substantially alter the ligase step 3 activity. In other embodiments, the K159S mutant is encoded by the amino acid sequence SEQ ID NO:2 or a variant of this sequences having 97-99% identity with this sequence, or having an N or C terminal truncation of this sequence that does not substantially alter the normal ligase step 3 activity. In particular embodiments, the T4 DNA ligase is encoded by SEQ ID NO: 2, but with one amino acid change (not at position 159) that does not substantially alter the ligase step 3 activity.

BRIEF DESCRIPTION OF THE DRAWINGS

FIG. 6 shows the amino acid sequence for T4 DNA ligase K159S mutant (SEQ ID NO:1).

FIG. 7 shows the amino acid sequence for T4 DNA ligase K159C mutant (SEQ ID NO:2).

FIG. 8 shows the amino acid sequence for T4 DNA ligase K159A mutant (SEQ ID NO:3).

DEFINITIONS

Figure 1:
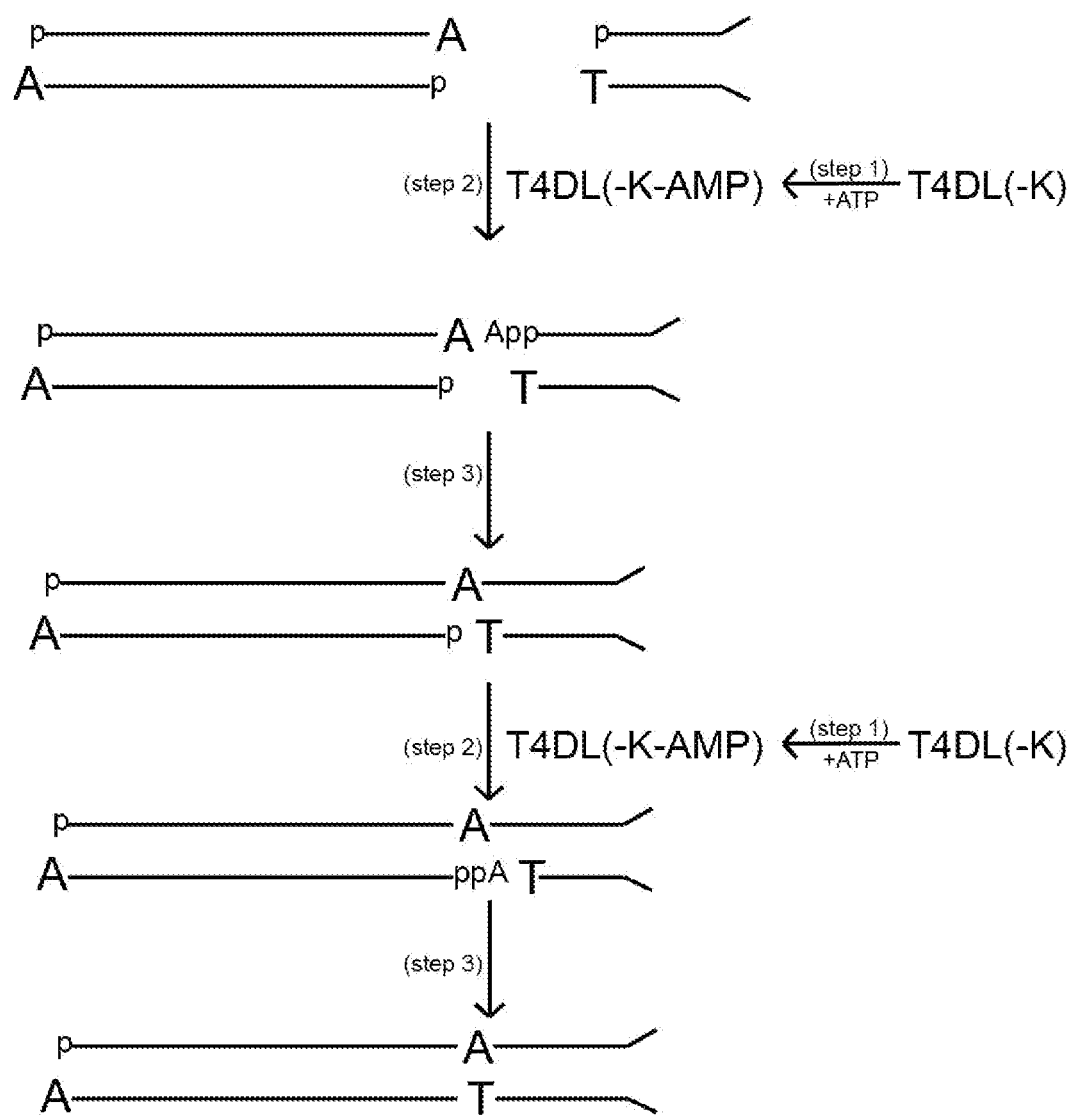
FIG. 1 shows an exemplary workflow depicting certain reaction steps in conventional ligation between A-tailed library DNA fragments and T-tailed adapter.

As used herein, the phrase "adenylation-deficient ATP-dependent ligase" refers to an ATP-dependent ligase that cannot form an AMP-ligase intermediate by reacting with ATP as normally done by ATP-dependent ligases. Examples of such DNA ligases include, but are not limited to, T4 DNA ligase K159S, K159C, and K159A mutants, as well as the K27A mutant from *Chlorella* virus PBCV-1 DNA ligase. Examples also include mutagenesis in other conserved motifs of ligases, such as R55K, K227Q and K225R in the T4 RNA ligase 2 (Yin et al., J Biol Chem 2003, 278:17601-17608, herein incorporated by reference in its entirety, particularly for such mutants). Other examples of adenylation-deficient ATP-dependent ligases include ATP-dependent ligases where the lysine within KxDG (Motif I) of the ligase is mutated to one of the other 19 amino acids such that the ligase is adenylation deficient but step 3 ligase competent. Such mutants can be generated and screened for adenylation deficiency, and step 3 ligase competence, using the methods shown, for example, in the Examples section below.

As used herein, the phrase "an un-adenylated ATP-dependent ligase" refers to an ATP-dependent ligase that is able to form the normal AMP-ligase intermediate by reaction with ATP, but has not formed such an AMP-ligase intermediate (e.g., as it is present in an ATP free mixture).

DETAILED DESCRIPTION

Provided herein are compositions, systems, and methods using multiple ligases, wherein at least one of the ligases is an adenylation-deficient ATP-dependent ligase or an un-adenylated ATP-dependent ligase (e.g., present in an ATP free mixture). In certain embodiments, multiple ligases are used to ligate a pre-adenylated double stranded sequence to a non-adenylated double stranded sequence (e.g., the adenylation-deficient ATP-dependent ligase or un-adenylated ATP-dependent ligase ligates the first strand, and a different ligase ligates the second strand). In other embodiments, provided herein are mutant T4 ligases (e.g., K159S mutant or K159C mutant).

In a typical library preparation workflow, such as for the ILLUMINA platform (or other next generation sequencing platforms), large-sized DNA is first fragmented into smaller pieces. The heterogeneous ends of the fragmented DNA are repaired to blunt ends by a mixture of enzymes, followed by an extension of an extra A-base at the 3'-ends, for example, by utilizing the non-template dependent polymerization activities of the Taq polymerase (Clarks J M, NAR, 1988, herein incorporated by reference). The A-tailed DNA fragments are then ligated with double-stranded oligonucleotide adapters with complementary 3'-T overhangs. The ligation reaction is usually catalyzed by T4 DNA ligase alone to join both strands at the T/A junction. Since the ligation between the complementary single-base T- and A-ends is generally inefficient, the ligation reaction is usually supplemented with excess amount of ligase enzymes, as well as ligation enhancers, such as PEG8000 or other molecules (see, U.S. Pat. No. 8,697,408, herein incorporated by reference). The ligation between the A-tailed library DNA fragments and T-tailed adapters ensures that the ligation is directional between library DNA fragments and adapters, and there are minimal unwanted ligation products within library DNA fragments themselves or adapters themselves.

Ligation between blunt-ended library DNA fragments and adapters is also used in the library preparation workflow for high-throughput sequencing. For example, in the library preparation workflow for the PACBIO (Pacific Biosciences, CA) platform, large-sized DNA is fragmented into controlled sizes first. The ends of the fragmented DNA are repaired to blunt ends and ligated with 5'-phosphorylated blunt-ended adapters (Pacific Biosciences manual PN 001-143-835-08). Again, this ligation is catalyzed by only the T4 DNA ligase to join both strands at the blunt-end junction. Unwanted ligation products such as adapter dimers can form, but can be removed efficiently by size selection, such as by using AMPure beads (Beckman Coulter). Other unwanted ligation products, such as concatemers between library fragments may also form. However, given the excess amount of adapters to the library fragments, the fraction of such products is considered to be small.

A typical ligation reaction between the DNA library fragments and adapters generally requires each ligase molecule to carry out multiple rounds of ligation (i.e., multiple turn-over condition). To seal each strand break at the ligation junction, the ligases need to go through all 3 nucleotidyl transfer steps (see FIG. 1). However, the ligation of the first strand is much more challenging than that of the second strand, since the first ligation event involves joining of two separate double-stranded DNA molecules while the second ligation event occurs on an already connected, but nicked double-stranded substrate (FIG. 1). It can be expected that while the first ligation event generally requires the action of a ligase such as T4 DNA ligase, which is better at joining blunt ends and single-base overhangs, the second ligation can be catalyzed by other ATP-dependent or NAD-dependent DNA ligases, such as T7 DNA ligases, T3 DNA ligases, E. coli DNA ligases, PBCV-1 ligases etc. Because T4 DNA ligase itself is also efficient in catalyzing the double-stranded nick ligation, only T4 DNA ligase is used to catalyze both strand sealing rather than using a mixture of ligases.

From a reaction kinetics point of view at the ligation process, it has been observed that the reaction rate under single turn-over condition (enzyme>>substate) is much faster than that under multiple turn-over condition (enzyme<<substrate) for DNA ligases using double-stranded nicked DNA as substrate. Kinetic studies have suggested that either the product release from the enzyme (Lohman G J, J. Biol. Chem, 2011, herein incorporated by reference), which occurs after step 3, or enzyme adenylation (Wang Y et al, Biochemistry, 2007, herein incorporated by reference), which occurs in step 1, as the possible rate-limiting step to explain the difference. It has been observed that step 2, which is the nucleotidyl transfer step from adenylated ligase to the 5'-phorphorylated-end of the DNA, and step 3, which is the strand sealing step by the 3'-OH attack, occur relatively efficiently, with similar kinetics under single turn-over and multiple turn-over conditions. Therefore, while the present invention is not limited to any particular mechanism, and an understanding of the mechanism is not necessary to practice the invention, it is believed that, to improve the ligation efficiency, it is advantageous to bypass the rate-limiting steps and proceed directly with the fast kinetic steps. This may be accomplished, for example, by using a combination of enzymes, where the first ligase ligates a pre-adenylated first strand (e.g., using an adenylation-deficient ATP-dependent ligase and/or an un-adenylated ATP-dependent ligase), and a second ligase (e.g., any useful ligase) ligates the second strand.

In addition, it is also recognized that ligases may fall off the substrate after step 2, leaving an adenylated 5'-end on DNA. Once the ligase falls off the substrate after step 2, it can restart the step 1 again and undergo re-adenylation itself. Once the ligase is adenylated, it cannot re-bind to the adenylated 5'-end and catalyze the step 3 of the ligation, rendering such ends non-ligatable. To this end, supplementing 5'-deandelyase in the ligation reaction may help to rescuing such abortive ends by reversing the 5'-adenylated end to the 5'-phosphorylated end, thus increase the ligation yield over time (see, US Pat. Pub. 20150031026 and US Pat. Pub. 20150218608). However, it may be that the inclusion of 5'-deandenylase in the ligation reaction may interfere with normal ligation process by reversing excessive amount of 5'-adenylated ends.

It is conceivable to perform ligation reaction in separate nucleotidyl transfer steps in vitro (Shuman S., J. Bio. Chem, 2009, herein incorporated by reference). For example, step 1 occurs when ligases encounter co-factors such as ATP or NAD. Heterologous expression and purification of DNA ligases from expression hosts such as E. coli usually results in a mixture of adenylated and non-adenylated ligases. It is known in the art that ligases can be purified as the adenylated or non-adenylated form or as a mixture where one form is the majority (Lohman G J, JBC, 2011 and WO2010094040, both of which are incorporated by reference, and particularly with respect to purifying non-adenylated ligases). By using stoichiometric amounts of adenylated ligase, it is possible to only carry out the step 2 and 3 of the ligation and bypass the step 1 reaction (WO2010094040A1). Such reaction does not require the presence of co-factors such as ATP or NAD. However, to prepare adenylated ligase, extra steps during enzyme purification need to be taken and stoichiometric amount of enzyme is needed for the ligation reaction. Similarly, by using pre-adenylated 5'-end, steps 1 and 2 can be bypassed and step 3 ligation can be performed directly between the pre-adenylated 5'-end and 3'-OH end under the catalysis of non-adenylated ligases in the absence of ATP. The 5'-adenylated end, the product of the second ligation step, can be, for example, synthesized by enzymatic or chemical methods (e.g., Torchia, Nucl. Acids, Res, 2008, herein incorporated by reference, and particularly with respect to preparing adenylated nucleic acid). Multiple ways to perform the "split" ligation has gained increased popularity for RNA ligation in the RNA research field (Lau N C, Science, 2001; Zhelkovsky A M, BMC Mol Bio, 2012).

Besides wild-type non-adenylated DNA ligases, it is also possible to obtain adenylation-deficient but step-3-proficient DNA ligase mutants. For example, adenylation-deficient DNA ligases can be obtained through mutagenesis of the wild-type T4 DNA ligase. On the sequence level, the ATP-dependent ligases are defined by a set of six short conserved motifs (I, III, IIIa, IV, V and VI) (Shuman S, Mol. Microbio., 1995, herein incorporated by reference). The active site lysine residue to which AMP becomes covalently linked is located within the conserved motif I (Kx(D/N)G), where x is any amino acid. Mutation of the conserved Lysine to alanine in PBCV-1 DNA ligase (K27A) blocks the transfer of the adenyl group and renders the enzyme unable to adenylate itself. However, the mutant enzyme is still able to catalyze step 3 of the ligation reaction (Sriskanda V. et al, NAR, 1998, herein incorporated by reference in its entirety). In T4 DNA ligase, Lysine 159 is the catalytic lysine in motif I. Previous research has shown that mutation of the conserved Lysine159 to leucine in T4 DNA ligase abolishes its overall ligation activity (Ross R., et al, NAR, 1997).

Figure 2:
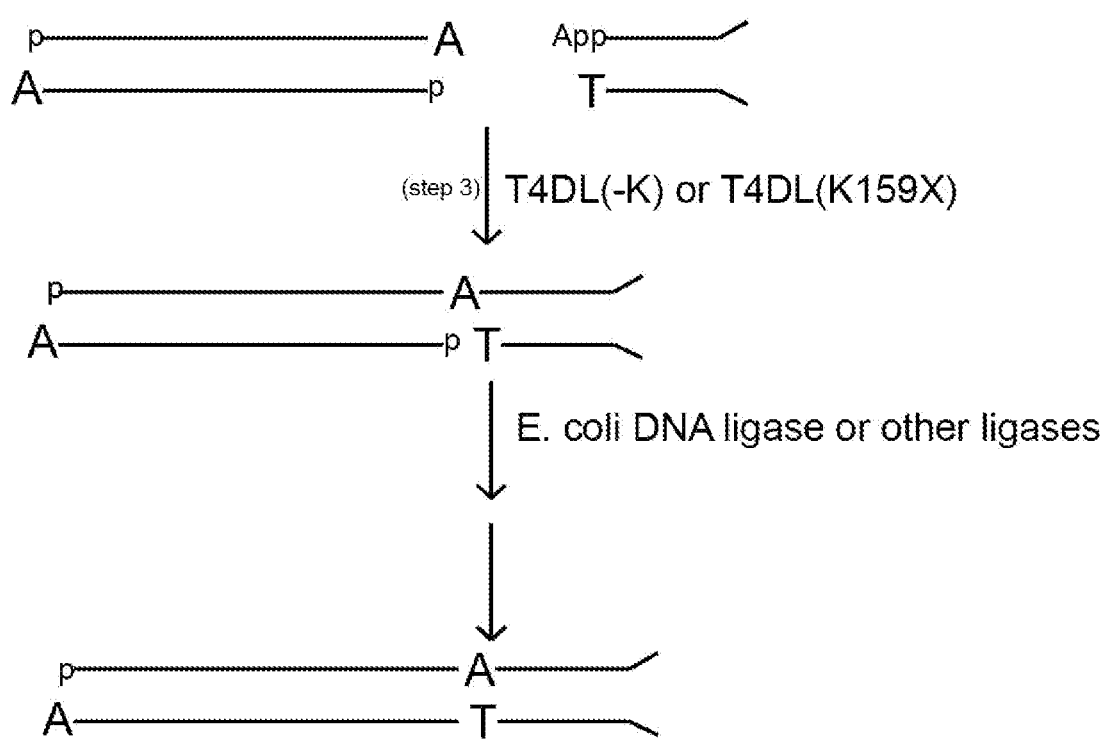
FIG. 2 is an exemplary, non-limiting embodiment, of only using step 3 for the first strand ligation (e.g., using an adenylation-deficient ATP-dependent ligase, or an un-adenylated ATP-dependent ligase) and another ligase for the second strand ligation for the A-tailed DNA fragments and adenylated T-tailed adapter.

In certain embodiments of the present disclosure, by using pre-adenylated double-stranded adapters (or other pre-adenylated double stranded nucleic acid sequences), the rate-limiting steps in double-stranded DNA ligation can be bypassed, and the relatively fast step 3 ligation in the first strand ligation (FIG. 2) can be performed. For example, as depicted in FIG. 2, double-stranded 3'-T-tailed adapters can be adenylated (e.g., using enzymatic or chemical methods). First strand ligation between A-tailed DNA fragments and adenylated adapter can be catalyzed by, for example, un-adenylated wild-type ligase (e.g., wild-type T4 DNA ligase) in the absence of ATP, or adenylation-deficient DNA ligase (e.g., T4 DNA ligase mutants or mutant PBCV-1 DNA ligase). In certain embodiments, T4 DNA ligase is employed for the first strand ligation as it is efficient in ligating blunt ends and single-base overhangs. Once the first strand is joined, second strand ligation can be performed using other ligases, such as T7, T3, E. coli, Taq, PBCV-1 ligases etc. Thus, instead of using only one ligase to perform both strand ligation, a ligase mixture can be used to separately ligate each strand.

While the present invention is not limited to any particular mechanism, and an understanding of the mechanism is not necessary to practice the invention, it is believed that there are several advantages to using a mixture of multiple different ligases to catalyze separate strand sealing. First, in the first strand ligation, potentially rate-limiting steps 1 and 2 have been bypassed, so that a faster kinetics is believed to be expected. Second, for the second strand nick-sealing ligation, there is a wide-selection of ligases that can be used without interfering with the first strand ligation. For example, the NAD-dependent E. coli ligase is relatively inert in ligating blunt or single-base ends but efficient in ligating double-stranded nicks. By using E. coli ligase as the second strand ligase, it is possible to eliminate the requirement of ATP for the overall ligations, which can be useful for certain applications. Third, as discussed below, since the first ligation is directional between the 3'-OH ends of the nucleic acid fragments and the 5'-adenylated ends of the adapters, and since the second strand ligase only catalyzes nick sealing, it is possible to minimize the unwanted ligation within nucleic acid fragments in blunt-end ligation.

In general, when using ATP-dependent DNA ligases for the second strand ligation in the methods herein, this normally requires ATP in the reaction, which may interfere with the first strand ligation if un-adenylated ligase is used (e.g., wild-type T4 ligase). Thus, in certain embodiments, if ATP-dependent DNA ligases are used for the second strand ligation, adenylation-deficient mutant ligases (e.g., mutant T4 DNA ligase mutants) are used for the first strand ligation. Alternatively, if an NAD+ dependent ligase is used for second strand ligation (e.g., E. coli DNA ligase), either un-adenylated wild-type ligase or adenylation-deficient ligase mutant can be used for the first strand ligation. Therefore, in some embodiments, one can use a combination of mixture of ligases in one pot to perform the first and second strand ligation.

Figure 3:
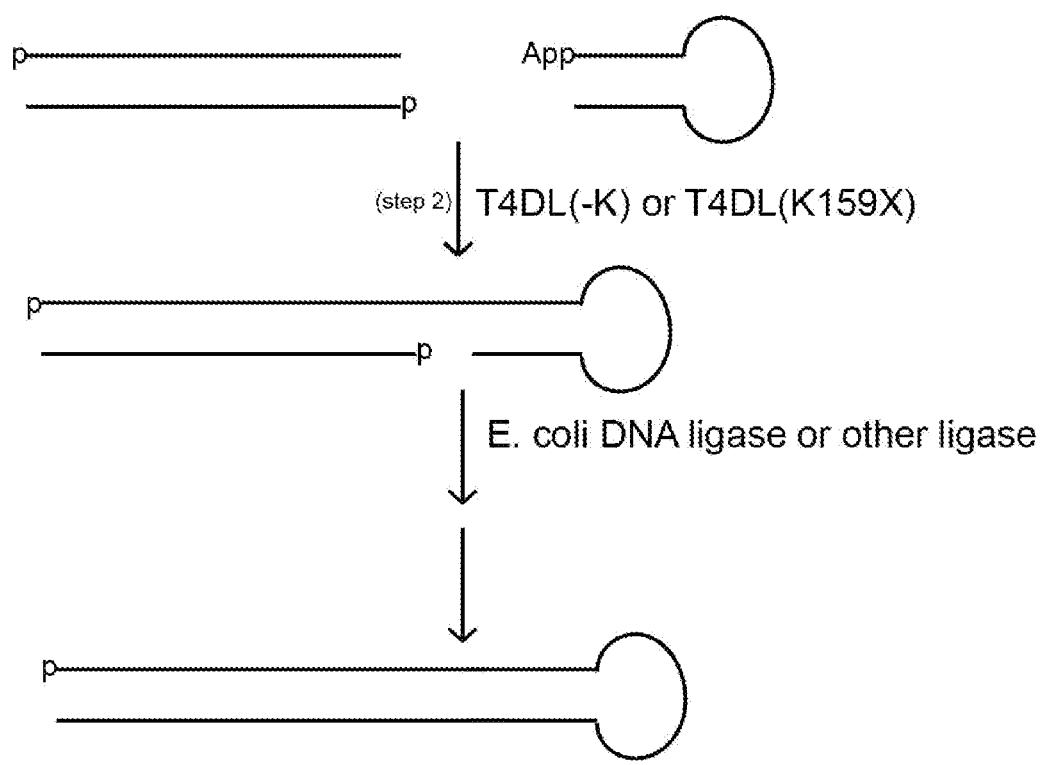
FIG. 3 is an exemplary, non-limiting embodiment, of only using step 3 for the first strand ligation (e.g., using an adenylation-deficient ATP-dependent ligase, or an un-adenylated ATP-dependent ligase) and another ligase for the second strand ligation for the blunt-end DNA fragments and adenylated blunt-end adapter.

As depicted in FIG. 3, blunt-end ligation between library DNA fragments and adapters can be performed using ligase mixtures as well. For example, first strand ligation between DNA library fragments and adenylated adapters can be catalyzed by un-adenylated ligases (e.g., T4 DNA ligases) in the absence of ATP, or adenylation-deficient ligase mutants (e.g., T4 DNA ligase mutants). Second strand ligation can be performed using other DNA ligases, such as T7, T3, E. coli, Taq DNA ligases etc. using the same combination guidelines outlined above. Since the ligation is directional from the adapter to the library fragment, compared with the traditional blunt-end ligation, a major advantage is that unwanted ligation products formed within the library DNA fragments are generally avoided. Adaptor dimers may form, but can be removed efficiently by, for example, size selection, for example, by using AMPure beads. As a result, by using proposed directional blunt-end ligation in the library preparation workflow, it is possible to avoid the A-tailing step, which has different efficiency in various sequencing contexts (see, Magnuson V L et al, Biotechniques, 1996) and could bring bias in sequencing results, and the single-base T-A ligation, which is generally less efficient than the blunt-end ligation.

As described in the Examples below, all 19 mutants of lysine 159 of T4 DNA ligase were tested in a step-3 ligation assay between blunt-end PCR fragment and adenylated blunt-end adapters. This data suggests that not all the lysine mutants are active in step-3 ligation (including the previously studied K159L). The Example identified at least three active adenylation-deficient, step-3-proficient lysine mutants with efficiency ranking of K159S>K159C>K159A. Given the nature of the amino acid side chains of lysine and serine, it is surprising that K159S mutant appears to have the highest level of activity in catalyzing step 3 of the ligation.

In certain embodiments, one may use adenylation-deficient, step-3-proficient mutants with DNA ligases in regular ligation reactions, thanks to their ability to finish the step-3 ligation once an adenylated 5'-end is generated. For example, it is recognized that ligases may fall off the substrate after the step 2, leaving an adenylated 5'-end on DNA. 5'-adenylated ends can be recognized and proceed to strand sealing by the adenylation-deficient, step-3-proficient ligase mutants. Compared with supplementing with 5'-deadenylase (US Pat. Pub. 20150031026), this approach does not reverse the reaction.

In certain embodiments, the multiple ligase mixtures and/or mutant ligases are used in sequencing methods, such as in attaching adapters to library fragments for subsequent sequencing. For example, in some embodiments, the disclosure provided herein finds use in a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), semiconductor sequencing, massive parallel clonal, massive parallel single molecule SBS, massive parallel single molecule real-time, massive parallel single molecule real-time nanopore technology, etc. Morozova and Marra provide a review of some such technologies in *Genomics*, 92: 255 (2008), herein incorporated by reference in its entirety.

Any number of DNA sequencing techniques are suitable, including fluorescence-based sequencing methodologies (See, e.g., Birren et al., Genome Analysis: Analyzing DNA, 1, Cold Spring Harbor, N.Y.; herein incorporated by reference in its entirety). In some embodiments, the present disclosure finds use in automated sequencing techniques understood in that art. In some embodiments, the present technology finds use in parallel sequencing of partitioned amplicons (PCT Publication No: WO2006084132, herein incorporated by reference in its entirety). In some embodiments, the technology finds use in DNA sequencing by parallel oligonucleotide extension (See, e.g., U.S. Pat. Nos. 5,750,341, and 6,306,597, both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803; all of which are herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; all of which are herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., *Clinical Chem.*, 55: 641-658, 2009; MacLean et al., *Nature Rev. Microbiol.*, 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), Life Technologies/Ion Torrent, the Solexa platform commercialized by Illumina, GnuBio, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing (Voelkerding et al., *Clinical Chem.*, 55: 641-658, 2009; MacLean et al., *Nature Rev. Microbiol.*, 7: 287-296; U.S. Pat. Nos. 6,210,891; 6,258,568; each herein incorporated by reference in its entirety), template DNA is fragmented, end-repaired, ligated to adapters, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., *Clinical Chem.*, 55: 641-658, 2009; MacLean et al., *Nature Rev. Microbiol.*, 7: 287-296; U.S. Pat. Nos. 6,833,246; 7,115,400; 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 250 nucleotides, with overall output exceeding 1 billion nucleotide pairs per analytical run.

Sequencing nucleic acid molecules using SOLiD technology (Voelkerding et al., *Clinical Chem.*, 55: 641-658, 2009; MacLean et al., *Nature Rev. Microbiol.*, 7: 287-296; U.S. Pat. Nos. 5,912,148; 6,130,073; each herein incorporated by reference in their entirety) also involves fragmentation of the template, ligation to oligonucleotide adapters, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specific color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, the technology descried herein finds use in nanopore sequencing (see, e.g., Astier et al., J. Am. Chem. Soc. 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, the technology described herein finds use in HeliScope by Helicos BioSciences (Voelkerding et al., Clinical Chem., 55: 641-658, 2009; MacLean et al., Nature Rev. Microbiol., 7: 287-296; U.S. Pat. Nos. 7,169,560; 7,282,337; 7,482,120; 7,501,245; 6,818,395; 6,911,345; 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics is used. The per-base accuracy of the Ion Torrent sequencer is ~99.6% for 50 base reads, with ~100 Mb to 100 Gb generated per run. The read-length is 100-300 base pairs. The accuracy for homopolymer repeats of 5 repeats in length is ~98%. The benefits of ion semiconductor sequencing are rapid sequencing speed and low upfront and operating costs.

The technology disclosed herein finds use in another nucleic acid sequencing approach developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, which is incorporated herein in its entirety.

Other single molecule sequencing methods include real-time sequencing by synthesis using a VisiGen platform (Voelkerding et al., Clinical Chem., 55: 641-58, 2009; U.S. Pat. No. 7,329,492; U.S. patent application Ser. No. 11/671, 956; U.S. patent application Ser. No. 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

In certain embodiments, provided herein are compositions, kits, and systems comprising a T4 DNA ligase K159S mutant encoded by SEQ ID NO:1, or encoded by a sequence with substantial identity with SEQ ID NO:1, and/or a T4 DNA ligase K159C mutant encoded by SEQ ID NO:2, or encoded by a sequence with substantial identity with SEQ ID NO:2. As applied to such polypeptides, the term "substantial identity" means that two peptide sequences, when optimally aligned, such as by the programs GAP or BESTFIT using default gap weights, share at least 80 percent sequence identity, or at least 90 percent sequence identity, or at least 95 percent sequence identity or more (e.g., 95% . . . 97% . . . or 99% percent sequence identity). In particular embodiments, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. In some embodiments, the conservative amino acids substitution groups are: valine-leucine-isoleucine, phenylalanine-tyrosine, lysine-arginine, alanine-valine, and asparagine-glutamine. In certain embodiments, provided herein are peptides that have substantial identity to at least a portion of the amino acid sequences shown in SEQ ID NOS: 1 and 2.

EXPERIMENTAL

Example 1

Identification of Active Adenylation-Deficient, Step-3-Proficient T4 DNA Ligase Mutants Wild-type T4 DNA ligase (T4DL) was synthesized using optimized *E. coli* codon with a N-terminal 6×His tag. The synthetic gene was cloned into T7-promoter driven expression vector pTXB1 (NEB). PCR-based mutagenesis using pTXB1_T4DLWT as template was done to change Lysine 159 to all the other 19 amino acids. All mutant expression vectors were sequence verified to confirm the expected change. Each mutant was then expressed in T7 Express strain (#C2566, NEB). Briefly, each 6 ml culture was first grown to O.D. ~0.6, IPTG induced to a final concentration of 0.5 mM, and shaken overnight at 20° C. Expression culture was then spun down, re-suspended in 450 ul buffer containing 20 mM Tris (pH=7.5), 150 mM NaCl, 1× Fast-Break (Promega), 200 ug/ml lysozyme, and sonicated. Cell lysates were then centrifuged at 14,000 rpm for 30 min at 4° C. Cleared lysates were loaded onto Ni-NTA bead column and target protein was eluted using elution buffer containing 20 mM Tris(pH=7.5), 150 mM NaCl, 400 mM imidazole.

Figure 4:
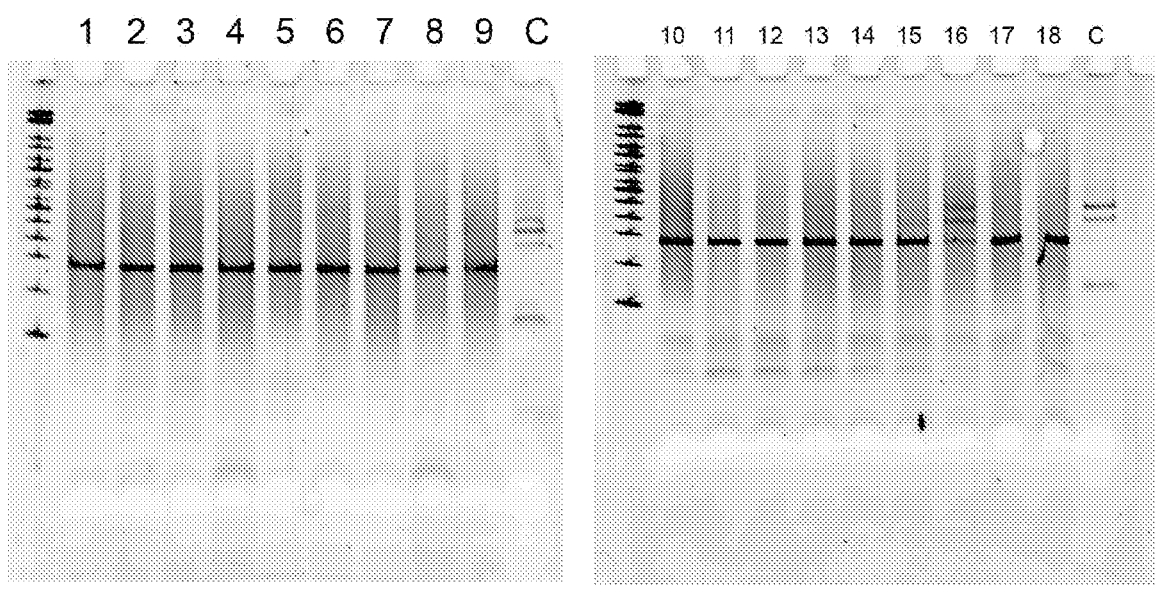
FIG. 4 shows results from Example 1 where the activity of T4 DNA ligase K159X mutants were tested in the step 3 reaction of ligation. Reaction was done in buffer with 70 mM Tris-HCl, 10 mM MgCl$_2$, 5 mM DTT pH 7.6 at 25° C. Each 10 ul reaction contained 0.2 ul blunt-ended PCR fragment and 0.2 ul adenylated blunt-end adapter. Reactions were incubated at room temperature for 1 hour, then subjected to proteinase K digestion for 1 hour at 50 C. Reactions were then run on 10% TBE gel, stained with SYBR Gold, and scanned on GE ImageQuant for visualization. The lanes in the gels are as follows: C) positive control reaction with wild-type T4 DNA ligase (NEB cat #: M0202L); 1) K159Y; 2) K159W; 3) K159P; 4) K159R; 5) K159D; 6) K159N; 7) K159T; 8) K159Q; 9) K159A; 10) K159E; 11) K159H; 12) K159V; 13) K159F; 14) K159I; 15) K159C; 16) K159S; 17) K159G; and 18) K159M.

For the step 3 ligation assay, blunt-end adaptor was synthesized from IDT (5'-GATCGGAAGAGCACACGTCTGAACTCCAGTC/ideoxyU/ACACTCTTTCCCTACACGAC GCTCTTCCGATC-3' SEQ ID NO:4), then phosphorylated using T4 polynucleotide kinase (NEB), and adenylated using 5'-adenylation kit according to manufacturer's instructions (NEB). A short PCR fragment (~250 bp) was amplified from pBR322 vector using Phusion DNA polymerase and purified. The step 3 ligation reaction was carried out in buffer containing 70 mM Tris-HCl, 10 mM MgCl2, 5 mM DTT. Each reaction contains 0.2 ul PCR fragment (~60 ng/ul) and 0.2 ul adenylated adaptor (~6 uM). All reactions were incubated at room temperature (25° C.) for 1 hour, after which 1 ul proteinase K (NEB) was added to each reaction followed by further incubation for 1 hour at 50° C. The reactions were then run on 10% TBE gel, stained with SYBR Gold and visualized. From FIG. 4, it can be observed that majority of the lysine mutants do not show significant step 3 ligation activity. K159S exhibits the strongest ligation activity, compared to other ligase mutants, followed by K159C and K159A.

Figure 5:
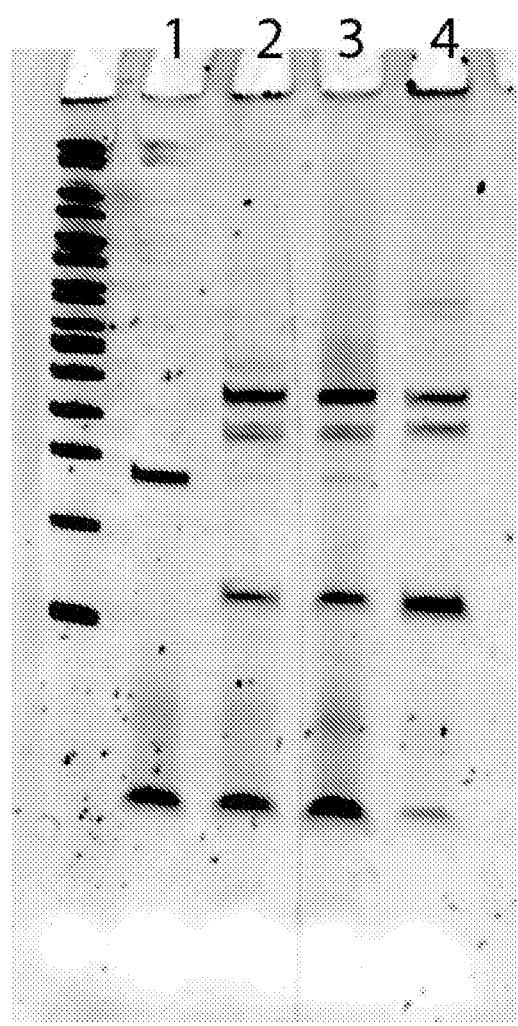
FIG. 5 shows results from Example 1 where blunt-end ligation was tested using various ligase mixtures. The lanes in the gel are as follows: Lane 1, PCR fragment and adapter only; lane 2, with K159S; lane 3, with K159S and *E. coli* ligase; lane 4, ligation of PCR fragment and phosphorylated blunt adapter using T4 DNA ligase.

To test blunt end ligation using ligase mixture, reactions were set up using ligase mixture and compared with regular ligation using T4 DNA ligase only. As shown in FIG. 5, lane 1 shows the ligation between blunt-end PCR fragment and adenylated blunt-end adaptor using K159S mutant only, lane 2 shows the same ligation using ligase mixture of K159S and *E. coli* ligase. In both cases, the ligation approaches to completion. Lane 4 shows the ligation between blunt-end PCR fragment and phosphorylated adaptor using T4 DNA ligase only. Although with similar efficiency, it can be seen that there are extra high-molecular bands formed, which could be from the concatenation of PCR fragments.

REFERENCES

Clark J M. Novel non-templated nucleotide addition reactions catalyzed by procaryotic and eucaryotic DNA polymerases. Nucleic Acids Res. 1988, 16(20):9677-86.

Lau N C, Lim L P, Weinstein E G, Bartel D P. An abundant class of tiny RNAs with probable regulatory roles in *Caenorhabditis elegans*. Science. 2001, 294(5543):858-62.

Lehman I R. DNA ligase: structure, mechanism, and function. Science. 1974 Nov. 29; 186(4166):790-7.

Lindahl T, Barnes D E. Mammalian DNA ligases. Annu Rev Biochem. 1992; 61:251-81.

Lohman G J, Chen L, Evans T C Jr. Kinetic characterization of single strand break ligation in duplex DNA by T4 DNA ligase. J Biol Chem. 2011 Dec. 23; 286(51):44187-96.

Magnuson V L, Ally D S, Nylund S J, Karanjawala Z E, Rayman J B, Knapp J I, Lowe A L, Ghosh S, Collins F S. Substrate nucleotide-determined non-templated addition of adenine by Taq DNA polymerase: implications for PCR-based genotyping and cloning. Biotechniques. 1996 October; 21(4): 700-9.

Rossi R, Montecucco A, Ciarrocchi G, Biamonti G. Functional characterization of the T4 DNA ligase: a new insight into the mechanism of action. Nucleic Acids Res. 1997, 25(11):2106-13.

Shuman S, Schwer B. RNA capping enzyme and DNA ligase: a superfamily of covalent nucleotidyl transferases. Mol Microbiol. 1995, 17(3):405-10.

Shuman S. DNA ligases: progress and prospects. J Biol Chem. 2009, 284(26):17365-9.

Sogaramella V, Khorana H G. Studies on polynucleotides. CXVI. A further study of the T4 ligase-catalyzed joining of DNA at base-paired ends. J Mol Biol. 1972, 72(3):493-502.

Sriskanda V, Shuman S. *Chlorella* virus DNA ligase: nick recognition and mutational analysis. Nucleic Acids Res. 1998, 26(2):525-31.

Torchia C, Takagi Y, Ho C K. Archaeal RNA ligase is a homodimeric protein that catalyzes intramolecular ligation of single-stranded RNA and DNA. Nucleic Acids Res. 2008, 36(19):6218-27.

Tomkinson A E, Vijayakumar S, Pascal J M, Ellenberger T. DNA ligases: structure, reaction mechanism, and function. Chem Rev. 2006, 106(2):687-99.

Wang Y, Lamarche B J, Tsai M D. Human DNA ligase IV and the ligase IV/XRCC4 complex: analysis of nick ligation fidelity. Biochemistry. 2007, 46(17):4962-76.

Weiss B, Richardson C C Enzymatic breakage and joining of deoxyribonucleic acid, I. Repair of single-strand breaks in DNA by an enzyme system from *Escherichia coli* infected with T4 bacteriophage. Proc Natl Acad Sci USA. 1967 April; 57(4): 1021-1028.

Zhelkovsky A M, McReynolds L A. Structure-function analysis of *Methanobacterium thermoautotrophicum* RNA ligase—engineering a thermostable ATP independent enzyme. BMC Mol Biol. 2012, 13:24. doi: 10.1186/1471-2199-13-24.

All publications and patents mentioned in the specification and/or listed below are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope described herein.

We claim:

1. A method of ligating a nucleic acid sequence comprising:

(a) combining the following components into a reaction mixture:

(i) a first ligase, wherein the first ligase is a T4 DNA ligase mutant comprising the amino acid sequence of SEQ ID NO: 1 or the amino acid sequence of SEQ ID NO: 2;

(ii) an adenylated double-stranded nucleic acid sequence (ADSNAS); and (iii) a non-adenylated double stranded nucleic acid sequence (non-ADSNAS);

wherein the non-ADSNAS comprises a first strand hybridized to a second strand, and wherein combining the components is under conditions such that the first ligase ligates the first strand of the non-ADSNAS to the ADSNAS; and (b) adding a second ligase to the reaction mixture under conditions such that the second ligase ligates the second strand of the non-ADSNAS to the ADSNAS, wherein the second ligase is an ATP-dependent ligase or a NAD-dependent ligase.

2. The method of claim 1, wherein the second ligase is an ATP-dependent ligase selected from the group consisting of a T4 DNA ligase, a T7 DNA ligase, a T3 DNA ligase and a PBCV-1 DNA ligase.

3. The method of claim 1, wherein the second ligase is an NAD-dependent ligase selected from the group consisting of an *E. coli* DNA ligase, a *Thermus thermophiles* DNA ligase, and a *Thermus aquaticus* DNA ligase.

* * * * *

SEQUENCE LISTING

<160> NUMBER OF SEQ ID NOS: 24

<210> SEQ ID NO 1
<211> LENGTH: 487
<212> TYPE: PRT
<213> ORGANISM: Artificial sequence
<220> FEATURE:
<223> OTHER INFORMATION: Synthetic

<400> SEQUENCE: 1

```
Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
            20                  25                  30

Arg Val Tyr Arg Leu Thr Tyr Ser Arg Gly Leu Gln Tyr Tyr Ile Lys
        35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
            100                 105                 110

Leu Glu Cys Gly Ala Ser Val Ser Ile Ala Asn Lys Val Trp Pro Gly
        115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Ser Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
        195                 200                 205

Pro Glu Gly Val Leu Ile Asp Gly Glu Leu Val Tyr His Glu Gln Val
    210                 215                 220

Lys Lys Glu Pro Glu Gly Leu Asp Phe Leu Phe Asp Ala Tyr Pro Glu
225                 230                 235                 240

Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
            260                 265                 270

Glu Ala Gln Cys Met Lys Phe Gln Val Trp Asp Tyr Val Pro Leu Val
        275                 280                 285

Glu Ile Tyr Ser Leu Pro Ala Phe Arg Leu Lys Tyr Asp Val Arg Phe
    290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
            340                 345                 350

Gly Leu Trp Glu Asn Ala Arg Ser Lys Asn Leu Tyr Lys Phe Lys Glu
```

```
                    355                 360                 365
Val Ile Asp Val Asp Leu Lys Ile Val Gly Ile Tyr Pro His Arg Lys
                370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
                420                 425                 430

Ile Gly Lys Ile Leu Glu Cys Glu Cys Asn Gly Trp Leu Lys Ser Asp
                435                 440                 445

Gly Arg Thr Asp Tyr Val Lys Leu Phe Leu Pro Ile Ala Ile Arg Leu
            450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 2
<211> LENGTH: 487
<212> TYPE: PRT
<213> ORGANISM: Artificial sequence
<220> FEATURE:
<223> OTHER INFORMATION: Synthetic

<400> SEQUENCE: 2

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
                20                  25                  30

Arg Val Tyr Arg Leu Thr Tyr Ser Arg Gly Leu Gln Tyr Tyr Ile Lys
            35                  40                  45

Lys Trp Pro Lys Pro Gly Ile Ala Thr Gln Ser Phe Gly Met Leu Thr
    50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
                100                 105                 110

Leu Glu Cys Gly Ala Ser Val Ser Ile Ala Asn Lys Val Trp Pro Gly
            115                 120                 125

Leu Ile Pro Glu Gln Pro Gln Met Leu Ala Ser Ser Tyr Asp Glu Lys
    130                 135                 140

Gly Ile Asn Lys Asn Ile Lys Phe Pro Ala Phe Ala Gln Leu Cys Ala
145                 150                 155                 160

Asp Gly Ala Arg Cys Phe Ala Glu Val Arg Gly Asp Glu Leu Asp Asp
                165                 170                 175

Val Arg Leu Leu Ser Arg Ala Gly Asn Glu Tyr Leu Gly Leu Asp Leu
            180                 185                 190

Leu Lys Glu Glu Leu Ile Lys Met Thr Ala Glu Ala Arg Gln Ile His
    195                 200                 205

Pro Glu Gly Val Leu Ile Asp Gly Glu Leu Val Tyr His Glu Gln Val
210                 215                 220

Lys Lys Glu Pro Glu Gly Leu Asp Phe Leu Phe Asp Ala Tyr Pro Glu
```

```
              225                 230                 235                 240
Asn Ser Lys Ala Lys Glu Phe Ala Glu Val Ala Glu Ser Arg Thr Ala
                245                 250                 255

Ser Asn Gly Ile Ala Asn Lys Ser Leu Lys Gly Thr Ile Ser Glu Lys
                260                 265                 270

Glu Ala Gln Cys Met Lys Phe Gln Val Trp Asp Tyr Val Pro Leu Val
                275                 280                 285

Glu Ile Tyr Ser Leu Pro Ala Phe Arg Leu Lys Tyr Asp Val Arg Phe
                290                 295                 300

Ser Lys Leu Glu Gln Met Thr Ser Gly Tyr Asp Lys Val Ile Leu Ile
305                 310                 315                 320

Glu Asn Gln Val Val Asn Asn Leu Asp Glu Ala Lys Val Ile Tyr Lys
                325                 330                 335

Lys Tyr Ile Asp Gln Gly Leu Glu Gly Ile Ile Leu Lys Asn Ile Asp
                340                 345                 350

Gly Leu Trp Glu Asn Ala Arg Ser Lys Asn Leu Tyr Lys Phe Lys Glu
                355                 360                 365

Val Ile Asp Val Asp Leu Lys Ile Val Gly Ile Tyr Pro His Arg Lys
                370                 375                 380

Asp Pro Thr Lys Ala Gly Gly Phe Ile Leu Glu Ser Glu Cys Gly Lys
385                 390                 395                 400

Ile Lys Val Asn Ala Gly Ser Gly Leu Lys Asp Lys Ala Gly Val Lys
                405                 410                 415

Ser His Glu Leu Asp Arg Thr Arg Ile Met Glu Asn Gln Asn Tyr Tyr
                420                 425                 430

Ile Gly Lys Ile Leu Glu Cys Glu Cys Asn Gly Trp Leu Lys Ser Asp
                435                 440                 445

Gly Arg Thr Asp Tyr Val Lys Leu Phe Leu Pro Ile Ala Ile Arg Leu
                450                 455                 460

Arg Glu Asp Lys Thr Lys Ala Asn Thr Phe Glu Asp Val Phe Gly Asp
465                 470                 475                 480

Phe His Glu Val Thr Gly Leu
                485

<210> SEQ ID NO 3
<211> LENGTH: 487
<212> TYPE: PRT
<213> ORGANISM: Artificial sequence
<220> FEATURE:
<223> OTHER INFORMATION: Synthetic

<400> SEQUENCE: 3

Met Ile Leu Lys Ile Leu Asn Glu Ile Ala Ser Ile Gly Ser Thr Lys
1               5                   10                  15

Gln Lys Gln Ala Ile Leu Glu Lys Asn Lys Asp Asn Glu Leu Leu Lys
                20                  25                  30

Arg Val Tyr Arg Leu Thr Tyr Ser Arg Gly Leu Gln Tyr Tyr Ile Lys
                35                  40                  45

Lys Trp Pro Lys Pro Gly Ile Ala Thr Gln Ser Phe Gly Met Leu Thr
                50                  55                  60

Leu Thr Asp Met Leu Asp Phe Ile Glu Phe Thr Leu Ala Thr Arg Lys
65                  70                  75                  80

Leu Thr Gly Asn Ala Ala Ile Glu Glu Leu Thr Gly Tyr Ile Thr Asp
                85                  90                  95

Gly Lys Lys Asp Asp Val Glu Val Leu Arg Arg Val Met Met Arg Asp
```

100                 105                 110
Leu Glu Cys Gly Ala Ser Val Ser Ile Ala Asn Lys Val Trp Pro Gly
            115                 120                 125
Leu Ile Pro Glu Gln Pro Gln Met Leu Ala Ser Ser Tyr Asp Glu Lys
130                 135                 140
Gly Ile Asn Lys Asn Ile Lys Phe Pro Ala Phe Ala Gln Leu Ala Ala
145                 150                 155                 160
Asp Gly Ala Arg Cys Phe Ala Glu Val Arg Gly Asp Glu Leu Asp Asp
                165                 170                 175
Val Arg Leu Leu Ser Arg Ala Gly Asn Glu Tyr Leu Gly Leu Asp Leu
                180                 185                 190
Leu Lys Glu Glu Leu Ile Lys Met Thr Ala Glu Ala Arg Gln Ile His
            195                 200                 205
Pro Glu Gly Val Leu Ile Asp Gly Glu Leu Val Tyr His Glu Gln Val
            210                 215                 220
Lys Lys Glu Pro Glu Gly Leu Asp Phe Leu Phe Asp Ala Tyr Pro Glu
225                 230                 235                 240
Asn Ser Lys Ala Lys Glu Phe Ala Glu Val Ala Glu Ser Arg Thr Ala
                245                 250                 255
Ser Asn Gly Ile Ala Asn Lys Ser Leu Lys Gly Thr Ile Ser Glu Lys
                260                 265                 270
Glu Ala Gln Cys Met Lys Phe Gln Val Trp Asp Tyr Val Pro Leu Val
            275                 280                 285
Glu Ile Tyr Ser Leu Pro Ala Phe Arg Leu Lys Tyr Asp Val Arg Phe
            290                 295                 300
Ser Lys Leu Glu Gln Met Thr Ser Gly Tyr Asp Lys Val Ile Leu Ile
305                 310                 315                 320
Glu Asn Gln Val Val Asn Asn Leu Asp Glu Ala Lys Val Ile Tyr Lys
                325                 330                 335
Lys Tyr Ile Asp Gln Gly Leu Glu Gly Ile Ile Leu Lys Asn Ile Asp
                340                 345                 350
Gly Leu Trp Glu Asn Ala Arg Ser Lys Asn Leu Tyr Lys Phe Lys Glu
            355                 360                 365
Val Ile Asp Val Asp Leu Lys Ile Val Gly Ile Tyr Pro His Arg Lys
            370                 375                 380
Asp Pro Thr Lys Ala Gly Gly Phe Ile Leu Glu Ser Glu Cys Gly Lys
385                 390                 395                 400
Ile Lys Val Asn Ala Gly Ser Gly Leu Lys Asp Lys Ala Gly Val Lys
                405                 410                 415
Ser His Glu Leu Asp Arg Thr Arg Ile Met Glu Asn Gln Asn Tyr Tyr
                420                 425                 430
Ile Gly Lys Ile Leu Glu Cys Glu Cys Asn Gly Trp Leu Lys Ser Asp
            435                 440                 445
Gly Arg Thr Asp Tyr Val Lys Leu Phe Leu Pro Ile Ala Ile Arg Leu
            450                 455                 460
Arg Glu Asp Lys Thr Lys Ala Asn Thr Phe Glu Asp Val Phe Gly Asp
465                 470                 475                 480
Phe His Glu Val Thr Gly Leu
                485

<210> SEQ ID NO 4
<211> LENGTH: 64
<212> TYPE: DNA
<213> ORGANISM: Artificial sequence
<220> FEATURE:
<223> OTHER INFORMATION: Synthetic

<400> SEQUENCE: 4
gatcggaaga gcacacgtct gaactccagt cuacactctt tccctacacg acgctcttcc    60
gatc    64

<210> SEQ ID NO 5
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa=any amino acid
<220> FEATURE:
<221> NAME/KEY: MISC_FEATURE
<222> LOCATION: (3)..(3)
<223> OTHER INFORMATION: Xaa= D or N

<400> SEQUENCE: 5

Gly Xaa Xaa Gly
1

<210> SEQ ID NO 6
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa=any amino acid
<220> FEATURE:
<221> NAME/KEY: MISC_FEATURE
<222> LOCATION: (3)..(3)
<223> OTHER INFORMATION: Xaa=D or N

<400> SEQUENCE: 6

Pro Xaa Xaa Gly
1

<210> SEQ ID NO 7
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa=any amino acid
<220> FEATURE:
<221> NAME/KEY: MISC_FEATURE
<222> LOCATION: (3)..(3)
<223> OTHER INFORMATION: Xaa=D or N

<400> SEQUENCE: 7

Ala Xaa Xaa Gly
1

<210> SEQ ID NO 8
<211> LENGTH: 4
<212> TYPE: PRT
<213> ORGANISM: Artificial sequence
<220> FEATURE:
<223> OTHER INFORMATION: Synthetic -continued

```
<220> FEATURE:
<221> NAME/KEY: MISC_FEATURE
<222> LOCATION: (2)..(2)
<223> OTHER INFORMATION: Xaa=any amino acid
<220> FEATURE:
<221> NAME/KEY: MISC_FEATURE
<222> LOCATION: (3)..(3)
<223> OTHER INFORMATION: Xaa=D or N

<400> SEQUENCE: 8

Val Xaa Xaa Gly
1

<210> SEQ ID NO 9
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa=any amino acid
<220> FEATURE:
<221> NAME/KEY: MISC_FEATURE
<222> LOCATION: (3)..(3)
<223> OTHER INFORMATION: Xaa=D or N

<400> SEQUENCE: 9

Leu Xaa Xaa Gly
1

<210> SEQ ID NO 10
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa=any amino acid
<220> FEATURE:
<221> NAME/KEY: MISC_FEATURE
<222> LOCATION: (3)..(3)
<223> OTHER INFORMATION: Xaa=D or N

<400> SEQUENCE: 10

Ile Xaa Xaa Gly
1

<210> SEQ ID NO 11
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa=any amino acid
<220> FEATURE:
<221> NAME/KEY: MISC_FEATURE
<222> LOCATION: (3)..(3)
<223> OTHER INFORMATION: Xaa=D or N

<400> SEQUENCE: 11

Met Xaa Xaa Gly
1

<210> SEQ ID NO 12
```

```
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa=any amino acid
<220> FEATURE:
<221> NAME/KEY: MISC_FEATURE
<222> LOCATION: (3)..(3)
<223> OTHER INFORMATION: Xaa=D or N

<400> SEQUENCE: 12

Cys Xaa Xaa Gly
1

<210> SEQ ID NO 13
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa=any amino acid
<220> FEATURE:
<221> NAME/KEY: MISC_FEATURE
<222> LOCATION: (3)..(3)
<223> OTHER INFORMATION: Xaa=D or N

<400> SEQUENCE: 13

Phe Xaa Xaa Gly
1

<210> SEQ ID NO 14
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa=any amino acid
<220> FEATURE:
<221> NAME/KEY: MISC_FEATURE
<222> LOCATION: (3)..(3)
<223> OTHER INFORMATION: Xaa=D or N

<400> SEQUENCE: 14

Tyr Xaa Xaa Gly
1

<210> SEQ ID NO 15
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa=any amino acid
<220> FEATURE:
<221> NAME/KEY: MISC_FEATURE
<222> LOCATION: (3)..(3)
<223> OTHER INFORMATION: Xaa=D or N

<400> SEQUENCE: 15
```

Trp Xaa Xaa Gly
1

<210> SEQ ID NO 16
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa=any amino acid
<220> FEATURE:
<221> NAME/KEY: MISC_FEATURE
<222> LOCATION: (3)..(3)
<223> OTHER INFORMATION: Xaa=D or N

<400> SEQUENCE: 16

His Xaa Xaa Gly
1

<210> SEQ ID NO 17
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa=any amino acid
<220> FEATURE:
<221> NAME/KEY: MISC_FEATURE
<222> LOCATION: (3)..(3)
<223> OTHER INFORMATION: Xaa=D or N

<400> SEQUENCE: 17

Arg Xaa Xaa Gly
1

<210> SEQ ID NO 18
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa=any amino acid
<220> FEATURE:
<221> NAME/KEY: MISC_FEATURE
<222> LOCATION: (3)..(3)
<223> OTHER INFORMATION: Xaa=D or N

<400> SEQUENCE: 18

Gln Xaa Xaa Gly
1

<210> SEQ ID NO 19
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa=any amino acid
<220> FEATURE:
<221> NAME/KEY: MISC_FEATURE

```
<222> LOCATION: (3)..(3)
<223> OTHER INFORMATION: Xaa=D or N

<400> SEQUENCE: 19

Asn Xaa Xaa Gly
1

<210> SEQ ID NO 20
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa=any amino acid
<220> FEATURE:
<221> NAME/KEY: MISC_FEATURE
<222> LOCATION: (3)..(3)
<223> OTHER INFORMATION: Xaa=D or N

<400> SEQUENCE: 20

Glu Xaa Xaa Gly
1

<210> SEQ ID NO 21
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa=any amino acid
<220> FEATURE:
<221> NAME/KEY: MISC_FEATURE
<222> LOCATION: (3)..(3)
<223> OTHER INFORMATION: Xaa=D or N

<400> SEQUENCE: 21

Asp Xaa Xaa Gly
1

<210> SEQ ID NO 22
<211> LENGTH: 4
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa=any amino acid
<220> FEATURE:
<221> NAME/KEY: MISC_FEATURE
<222> LOCATION: (3)..(3)
<223> OTHER INFORMATION: Xaa=D or N

<400> SEQUENCE: 22

Ser Xaa Xaa Gly
1

<210> SEQ ID NO 23
<211> LENGTH: 4
<212> TYPE: PRT
<213> ORGANISM: Artificial sequence
<220> FEATURE:
<223> OTHER INFORMATION: Synthetic
<220> FEATURE:
```

```
<221> NAME/KEY: MISC_FEATURE
<222> LOCATION: (2)..(2)
<223> OTHER INFORMATION: Xaa=any amino acid
<220> FEATURE:
<221> NAME/KEY: MISC_FEATURE
<222> LOCATION: (3)..(3)
<223> OTHER INFORMATION: Xaa=D or N

<400> SEQUENCE: 23

Thr Xaa Xaa Gly
1

<210> SEQ ID NO 24
<211> LENGTH: 3
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa=any amino acid
<220> FEATURE:
<221> NAME/KEY: MISC_FEATURE
<222> LOCATION: (2)..(2)
<223> OTHER INFORMATION: Xaa=D or N

<400> SEQUENCE: 24

Xaa Xaa Gly
1
```